United States Patent [19]

Ratcliffe et al.

[11] 4,235,922
[45] Nov. 25, 1980

[54] 3-(2-AMINOETHYLTHIO)-6-ETHYL-7-OXO-1-AZABICYCLO[3.2.0]HEPT-2-ENE-2-CARBOXYLIC ACID

[75] Inventors: Ronald W. Ratcliffe, Matawan; Linda J. Ruswinkle, Rahway, both of N.J.

[73] Assignee: Merck & Co., Inc., Rahway, N.J.

[21] Appl. No.: 48,944

[22] Filed: Jun. 15, 1979

Related U.S. Application Data

[63] Continuation-in-part of Ser. No. 861,230, Dec. 16, 1977, abandoned, which is a continuation-in-part of Ser. No. 785,811, Apr. 8, 1977, abandoned.

[51] Int. Cl.³ .................. C07D 487/04; A61K 31/40
[52] U.S. Cl. ........................ 424/274; 260/245.2 T
[58] Field of Search ............. 260/326.31, 245.2 T; 424/274

[56] References Cited
FOREIGN PATENT DOCUMENTS 2815157 10/1978 Fed. Rep. of Germany .... 260/245.2 T
52-94651 8/1977 Japan ................................ 260/245.2 T

OTHER PUBLICATIONS

Schönberg et al.; J.A.C.S. vol. 100 p. 6491 (1978).
Okamura et al.; Jour. Of Centibiotics; vol. 31 No. 5 pp. 480–482 (5/1978).

*Primary Examiner*—Mary C. Lee
*Attorney, Agent, or Firm*—Frank M. Mahon; Julian S. Levitt

[57] ABSTRACT

The antibiotic 3-(2-Aminoethylthio)-6-ethyl-7-oxo-1-azabicyclo[3.2.0]hept-2-ene-2-carboxylic acid(I) and processes for its preparation are disclosed:

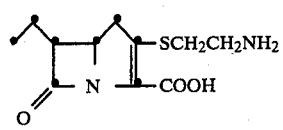

Also disclosed are pharmaceutical compositions comprising I and methods of treatment comprising administering I when an antibiotic effect is indicated.

8 Claims, No Drawings

3-(2-AMINOETHYLTHIO)-6-ETHYL-7-OXO-1-AZABICYCLO [3.2.0]HEPT-2-ENE-2-CARBOXYLIC ACID

BACKGROUND OF THE INVENTION

This is a continuation-in-part of co-pending U.S. Ser. No. 861,230, filed Dec. 16, 1977, now abandoned which in turn is a continuation-in-part of U.S. Ser. No. 785,811 filed Apr. 8, 1977, now abandoned.

This invention relates to 3-(2-aminoethylthio)-6-ethyl-7-oxo-1-azabicyclo[3.2.0]hept-2-ene-2-carboxylic acid (I) and its pharmaceutically acceptable salts which are useful as antibiotics:

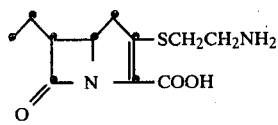

This invention also relates to processes for preparing I; pharmaceutical compositions comprising I and methods of treatment comprising administering I when an antibiotic effect is indicated.

3-(2-Aminoethylthio)-6-ethyl-7-oxo-1-azabicyclo[3.2.0]hept-2-ene-2-carboxylic acid (I) is conveniently derived from the antibiotic thienamycin (II) by removal of the 8-hydroxyl group:

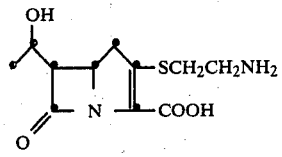

Thienamycin is disclosed and claimed in U.S. Pat. No. 3,950,357 issued Apr. 13, 1976, which patent is incorporated herein by reference since thienamycin may serve as a starting material for the preparation of the compounds of the present invention.

Thienamycin and all of its isomers (in pure form and as mixtures) are also obtainable by the total synthesis disclosed and claimed in co-pending, commonly assigned U.S. patent application Ser. No. 833,210 (Sept. 15, 1977), now abandoned. This application is incorporated herein by reference to the extent that it makes available all isomers of I as starting materials in the preparation of the compounds of the present invention.

This invention also relates to intermediates (III, IV) useful in the preparation of I:

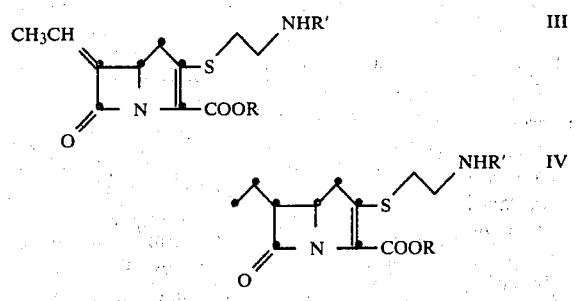

wherein R and R' are hydrogen or easily removable protecting groups; R and R' are defined in greater detail below.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel antibiotic and the pharmaceutically acceptable salts thereof which are useful in animal and human therapy and in inanimate systems. These antibiotics are active against a broad range of pathogens which representatively include both gram positive bacteria such as *S. aureus, Strep. pyogenes* and *B. subtilis,* and gram negative bacteria such as *E. coli, Proteus morganii,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

In general the compounds of the present invention are prepared according to the following scheme:

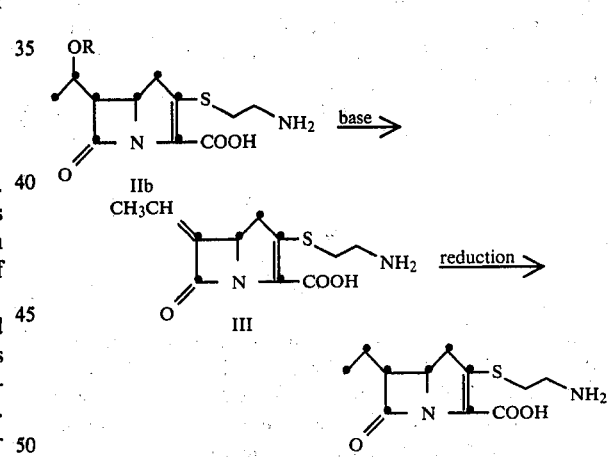

wherein the radical OR of structure IIb is easily eliminated on treatment with base to form the enelactam III which, upon reduction, yields the compound of the present invention, I. The radical OR is typically a sulfate or sulfonate.

More specifically, the 3-(2-aminoethylthio)-6-ethyl-7-oxo-1-azabicyclo[3.2.0]hept-2-ene-2-carboxylic acid of the present invention, I, is conveniently prepared by the following reaction scheme:

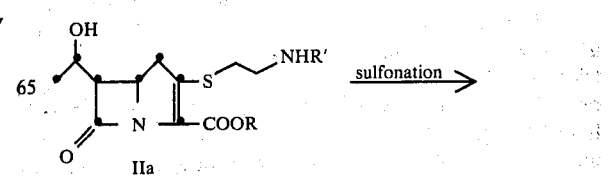

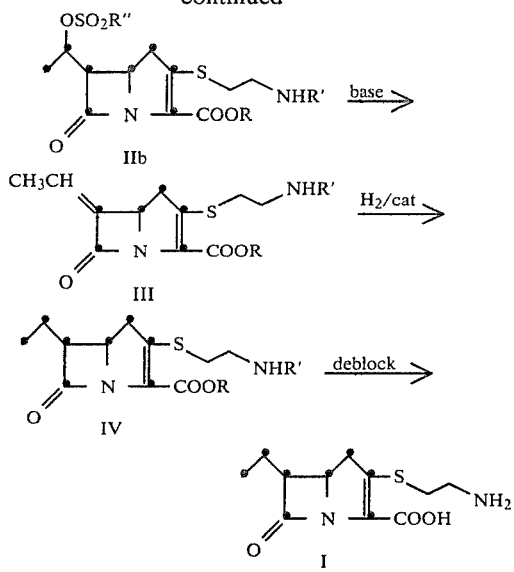

wherein R" is O⊖M⊕, M is hydrogen or any non-critical cation such as an alkali metal or organic base; or R" is alkyl or an aryl radical such as methyl or toluyl; and wherein R is a readily removable carboxyl blocking (or protecting) group and R' is a readily removable N-blocking group. Such blocked thienamycins, IIa, are disclosed in co-pending, commonly assigned U.S. patent application Ser. No. 733,655, filed Oct. 18, 1976, now abandoned in favor of U.S. patent application Ser. No. 861,234, filed Dec. 16, 1977. This application is incorporated herein by reference for its disclosure relative to the preparation of IIa. Preferred carboxyl-blocking groups, R, are benzyl and nuclear-substituted benzyl:

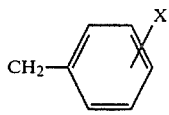

wherein X is nitro, lower alkoxyl such as methoxy, and the like; benzyl is preferred. Suitable N-blocking groups, R', include bromo-t-butoxycarbonyl, chloro-t-butoxycarbonyl, bromoethoxycarbonyl, benzyloxycarbonyl, p-nitrobenzyloxycarbonyl, and the like. An especially preferred N-blocking group is bromo-t-butoxycarbonyl.

In words relative to the above reaction diagram, a suitably protected thienamycin, IIa, is converted to the corresponding sulfonate or sulfate ester, IIb, by procedures which are disclosed in the above-cited and incorporated by reference U.S. patent application Ser. No. 733,655 filed Oct. 18, 1976, now abandoned. Typically, the intermediate species IIb as a sulfonate is prepared by treating IIa in a solvent such as methylene chloride, THF, dioxane, CHCl₃, or the like with a sulfonating agent such as methane sulfonyl chloride, toluene sulfonyl chloride or the like in the presence of base such as triethylamine, pyridine, 4-dimethylaminopyridine, NaH or the like at a temperature of from −15° to 25° C. for from 1 to 10 hours. Sulfate ester embodiments of intermediate species IIb (R" is —O⊖M⊕) are also suitable starting materials and have the following structural formula:

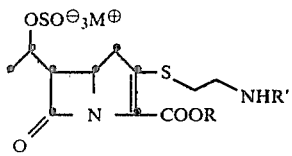

wherein M is hydrogen, an alkali metal cation or an organic base and R and R' are as defined above. Such sulfate ester embodiments are also disclosed in the above-cited and incorporated by reference U.S. patent application Ser. No. 733,655 filed Oct. 18, 1976, now abandoned in favor or U.S. patent application Ser. No. 861,234, filed Dec. 16, 1977.

It should be noted relative to the reaction involving intermediate species IIb that the groups R and R' may be, in addition to the above-named protecting groups, hydrogen. Such intermediate IIb species are prepared by deblocking the protected form of IIb according to conventional procedures which are described below.

It should be noted that sulfate ester embodiments of intermediate species IIb (R" is OH) are also obtainable as natural products. Such products are disclosed in commonly assigned, co-pending U.S. patent applications Ser. Nos. 767,723 and 767,920 both filed Feb. 11, 1977, both now abandoned in favor of U.S. patent applications Ser. Nos. 860,665 and 860,662, respectively both filed Dec. 15, 1977, and both now abandoned. These applications are incorporated herein by reference for their disclosure relative to the preparation and isolation of sulfate ester intermediate species IIb which are useful in the process of the present invention.

Relative to the above reaction diagram, the enelactam intermediate III is prepared from IIb by treating IIb with base such as NaHCO₃, K₂HPO₄, triethylamine, 1,5-diazabicyclo[5.4.0]undec-5-ene or the like in a solvent such as methanol, THF, dioxane or the like at a temperature of from −20° to 25° C. for 1 to 20 hours.

The 6-ethyl intermediate IV is obtained from III by reduction, preferably by treating III in a solvent such as ethanol, ethylacetate, dioxane, benzene or the like in the presence of a hydrogen catalyst such as PtO₂, RuO₂, Pt/C, or the like in the presence of 1 to 4 atmospheres of hydrogen at a temperature of from 0° to 25° C. for from 0.5 to 5 hours. Intermediate IV may be deblocked by the above-described hydrogenation procedure to obtain I or, depending upon the identity of the protecting groups R' and R, the deblocking may be accomplished by separate procedures such as hydrolysis or hydrogenation under different conditions. It should be again pointed out that deblocking may occur earlier in the scheme on intermediate species IIb. The deblocking procedure may also be accomplished as a single step reaction in the conversion of III→IV. Separate deblocking IV→I may be conducted by any of a variety of well-known procedures such as hydrolysis or hydrogenation. Preferably the carboxyl blocking group R is removed by hydrogenation in a solvent such as a loweralkanol, for example, ethanol in the presence of a hydrogenation catalyst such as palladium, platinum or oxides thereof under 1–40 atmospheres of hydrogen at from 0° to 50° C. for from 1 to 10 hours. The N-protecting group R' may also be removed by hydrogenation, but when the preferred bromo-t-butoxy carbonyl group is used the deblocking is conveniently achieved by heating a solution of IV or carboxyl-deblocked IV in a solvent such as ethanol, isopropanol, water or the like at 25°–80° C. for from 10 minutes to 3 hours.

Alternatively, the sulfonate intermediate IIb may be treated with sodium iodide in the presence of methyl ethyl ketone (MEK) to form the corresponding 6-(1-iodoethyl) intermediate IIIb which then may be reduced to the 6-ethyl intermediate IV (trans-configuration) with sodium cyanoborohydride in the presence of hexamethylphosphoramide (HMPA). Deblocking, by techniques described above, yields Compound I. This technique is illustrated below.

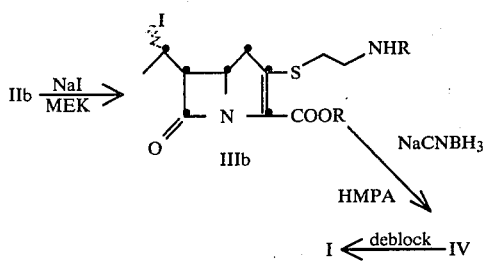

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-loweralkylamino substituted lower alkanols, amino-, polyamino- and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Salts of the primary amine of I with pharmaceutically acceptable organic and inorganic acids are also contemplated. Such salts include methanesulfonate, 2-naphthalenesulfonate, pamoate, 3-phenyl propionate, trimethylacetate, t-butyl acetate, p-toluenesulfonate, maleate, lactate, cyclamate, fumarate, tartrate, oxalate, benzoate, acetate, succinate, citrate, glutamate, hydrochloride, hydrobromide, sulfate, phosphate, n-acetyl-glycinate benzenesulfonate, hexanoate, p-chlorobenzenesulfonate, cyclopentanepropionate, 1,2-ethane disulfonate, gluroheptanoate, ethanesulfonate, o-(4-hydroxybenzoyl)benzoate, 2-hydroxyethanesulfonate, and the like; and are prepared according to well-known procedures.

The salts can be mono- salts such as the mono-sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit dosage pharmaceutical forms. Also, they may be combined with other drugs to provide compositions having a broad spectrum of activity.

The compounds of the present invention, I, and salts thereof are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa,* Pseudomones and *Bacterium proteus.* The antibacterials of the invention may further be utilized as additives to animal feeding stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oil or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intromammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention.

EXAMPLE 1

Preparation of N-Bromo-t-Butyloxycarbonyl Thienamycin Sodium Salt

Method A:

Thienamycin (190 mg) dissolved in 15 ml. 0.1 M phosphate buffer and 15 ml dioxane is kept at 0° C. The solution is adjusted and maintained between pH 8.5–9.0 with 1 N NaOH while 480 mg of bromo-t-butyl chloroformate is added to the solution during a period of 5 min. The mixture is stirred for 30 min, and then is neutralized to pH 7.0 with 1 N HCl and extracted with ether. The aqueous layer is separated, concentrated to 10 ml and chromatographed on a Dowex-50XB (Na Form) column (1.5"×10") which is eluted with $H_2O$ to give 113 mg of the desired product after lyophilization.

Method B:

Thienamycin (95 mg) in 10 ml 0.1 M phosphate buffer and 10 ml dioxane is kept at 0° C. The solution is adjusted and maintained between pH 8.5–9.0 while 240 mg of bromo-t-butyl chloroformate is added. The mixture is stirred for 30 min, and then is acidified to pH 2.0 with $H_3PO_4$. The acidified solution is extracted with 2×25 ml ethyl acetate. The organic layer is separated and back extracted with 10 ml of aqueous $NaHCO_3$ solution (solution contains 30 mg of $NaHCO_3$). The aqueous layer provides 30 mg of the desired product after lyophilization. NMR (60 MHz, $D_2O$): δ1.26 (d), 1.60 (s), 2.65–3.50 (m), 3.70 (s), and 3.90–4.20 (m). $UV\lambda^{D_2O}$ 303 nm.

EXAMPLE 2

Preparation of N-Bromo-t-Butyloxycarbonyl thienamycin p-nitrobenzyl ester

The lyophilized N-bromo-t-butyloxycarbonyl thienamycin sodium salt (100 mg) is stirred at 26° C. with p-nitrobenzyl bromide (300 mg) in 2 ml hexamethylphosphoramide for 1 hr. The mixture is diluted with 10 ml ethyl acetate and then washed thoroughly with water. The organic layer is separated, dried over $Na_2SO_4$ and chromatographed on two 250μ silica gel GF TLC plates using ethyl acetate as solvent ($R_f$ 0.45) to give 50 mg of the desired product. IR ($CDCl_3$): 1777 (β-lactam) and 1711 cm$^{-1}$ (ester); UV $\lambda_{max}^{EtOH}$ 270 nm and 322 nm; Nmr ($CDCl_3$, 60 MHz): δ1.38 (d), 1.58 (s), 2.60–3.80 (m), 3.78 (s), 3.90–4.20 (m), 5.30 (s), 7.55 (d) and 8.30 ppm (d).

The benzyl ester is obtained as above except an equivalent amount of benzyl bromide is substituted for the p-nitrobenzyl bromide of Example 2.

EXAMPLE 3

Preparation of N-Benzyloxycarbonyl thienamycin benzyl ester

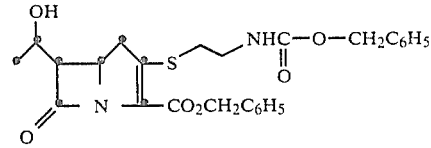

Thienamycin (214 mg, 0.79 mmol) is dissolved in ice-cold, deionized $H_2O$ (22 ml) and the solution is stirred with ice bath cooling; NaHCO$_3$ (995 mg, 11.85 mmol) is added all at once and stirring is continued for 5 minutes. Dioxane (17.6 ml) is then added and the solution is stirred 5 more minutes. An ice-cold solution of benzyl chloroformate (242 mg, 1.42 mmol) in THF (5 ml) is then added in 5 equal portions over 16 mins. After stirring 15 more minutes in the cold, the reaction mixture is layered with ice-cold diethylether (Et$_2$O) (40 ml) and acidified to pH 6.8 with cold 5% aqueous H$_3$PO$_4$. The layers are separated and the aqueous portion is extracted with more cold Et$_2$O (2×30 ml). The aqueous phase is layered with ice-cold ethylacetate (EtOAc, 35 ml) and the mixture is stirred rapidly with ice-bath cooling while the pH is brought to 2.4 with cold 10% aqueous H$_3$PO$_4$. The layers are separated and the aqueous portion extracted with more cold EtOAc (15 ml). The combined EtOAc solution is washed with ice-cold brine (20 ml) dried with Na$_2$SO$_4$ in the cold, and filtered. This solution contains N-benzyloxycarbonyl thienamycin.

Ice-cold, ethereal phenyldiazomethane (15 ml of a 0.25 M solution) is added to the EtOAc solution and the resulting solution is left in a refrigerator for one hour. The solvents are evaporated in vacuo and the residue is twice diluted with EtOAc and stripped in vacuo to remove dioxane. The residue is dissolved in EtOAc (5 ml) and the solution slowly diluted with Et$_2$O (5 ml). After storing in a refrigerator overnight, the mixture is filtered to remove the precipitate. This material is washed with cold Et$_2$O and dried in vacuo to yield N-benzyloxycarbonyl thienamycin benzyl ester (160 mg) as an off-white solid.

The mother liquors and washings are combined and evaporated in vacuo. The residue is triturated with hexane (3×50 ml), dissolved in EtOAc, and passed through a sintered glass funnel containing silica gel (2 g). The silica gel pad is washed with more EtOAc. The combined EtOAc eluant is evaporated in vacuo to about 1 ml, diluted with Et$_2$O to 5 ml., and left in a refrigerator for two days. The precipitate is collected, washed with cold Et$_2$O and dried in vacuo to yield additional N-benzyloxycarbonyl thienamycin benzyl ester (48 mg) as white flakes.

The first crop of product has: mp 125°–126° (micro hot stage); ir (CH$_2$Cl$_2$) 3608, 3424, 1780, 1720, 1514, 1332, 1206, and 1137 cm$^{-1}$; uv (dioxane) 317 ($\epsilon$11,800) nm; nmr (CDCl$_3$) $\delta$1.34 (d, 3, CH$_3$), 2.70–3.55 (m, 7, CH$_2$, SCH$_2$, NCH$_2$,H$_6$), 4.16 (m, 2, H5, H8), 5.10 (s, 2, NCO$_2$CH$_2\phi$), 5.29 (ABq, 2, CO$_2$CH$_2\phi$), and 7.32 (m, 10, ArH).

EXAMPLE 4

N-Benzyloxycarbonyl thienamycin benzyl ester

Thienamycin (798 mg, 2.93 mmol) is dissolved in ice-cold H$_2$O (200 ml) and the resulting solution is stirred with ice-bath cooling. Solid NaHCO$_3$ (2.462 g, 29.3 mmol) is added in one portion and, after a few minutes, dioxane (200 ml) is added. The resulting mixture is stirred in the cold for 3 minutes and then treated dropwise over 10 minutes with a solution of benzyl chloroformate (750 mg, 4.4 mmol) in anhydrous dioxane (12 ml). After stirring an additional 10 minutes in the cold, the reaction mixture is extracted with ice-cold Et$_2$O (2×120 ml). The aqueous portion is layered with cold EtOAc (100 ml) and vigorously stirred while acidifying to pH 2.3 with cold 1 M H$_2$SO$_4$. The layers are separated and the aqueous phase is extracted with additional cold EtOAc (2×30 ml). The combined EtOAc solution is washed with ice-cold brine (50 ml) and then extracted with ice-cold 0.05 N LiOH (58.6 ml). The aqueous LiOH extract is rotary evaporated in vacuo to remove EtOAc and then lyophilized to provide crude N-benzyloxycarbonyl thienamycin lithium salt (1.0 g) as a light yellow solid. A sample of the above lithium carboxylate (864 mg) is suspended in anhydrous hexamethylphosphoramide (HMPA) (15.7 ml) and treated with benzyl bromide (1.15 ml). The resulting mixture is stirred under N$_2$ and at 25° C., for 2 hrs then diluted with EtOAc (350 ml), and washed with H$_2$O (2×300 ml), 5% NaHCO$_3$ (150 ml), H$_2$O (2×150 ml), and brine (150 ml). The EtOAc solution is dried with MgSO$_4$, filtered and evaporated in vacuo to a gummy residue. This material is triturated with hexane (5×10 ml) to remove excess benzyl bromide and dried in vacuo to a light yellow solid (817 mg). The crude product is dissolved in warm EtOAc (15 ml) and diluted with Et$_2$O (15 ml). The resulting solution is seeded and left in a freezer overnight. The precipitate is collected, washed with cold Et$_2$O, and dried in vacuo to yield N-benzyloxycarbonyl thienamycin benzyl ester (405 mg) as an off-white solid.

The mother liquors and washings are evaporated in vacuo to an oily residue which is dissolved in warm EtOAc (~5 ml) and diluted with Et$_2$O (~10 ml). The solution is left in a freezer for several days to yield a second crop of product (106 mg) as a yellow solid.

EXAMPLE 5

N-Benzyloxycarbonyl O-methanesulfonyl thienamycin benzyl ester

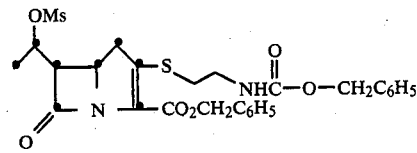

N-Benzyloxycarbonyl theinamycin benzyl ester (50 mg, 0.1 mmol) is dissolved in anhydous CH$_2$Cl$_2$ (3.0 ml) and the solution is stirred with ice-bath cooling under a N$_2$ atmosphere. Triethylamine (Et$_3$N) (27.9 $\mu$l, 0.2 mmol) is added to the solution followed by dropwise addition over 5 minutes of a solution of methanesulfonyl chloride (17.2 mg, 0.15 mmol) in CH$_2$Cl$_2$ (0.4 ml). The resulting solution is stirred in the cold for 90 minutes, then diluted with ice-cold CH$_2$Cl$_2$ (10 ml), washed with cold H$_2$O (5 ml), cold 0.1 M pH 3 phosphate buffer (2 ml) and cold 2% NaHCO$_3$ (5 ml), dried with MgSO$_4$, and filtered. Evaporation of the solvent in vacuo affords N-benzyloxycarbonyl O-methanesulfonyl thienamycin benzyl ester (57 mg) as a pale yellow oil: nmr (CDCl$_3$) 1.56 (d, 3, CHCH$_3$), 2.82–3.52 (m, 7, CH$_2$, SCH$_2$, NCH$_2$, H6), 3.00 (s, 3, CH$_3$SO$_2$), 4.28 (d of t, 1, H5), 5.08 (d of q, 1, H8), 5.09 (s, 2, NCO$_2$CH$_2\phi$), 5.26 (ABq, 2, CO$_2$CH$_2\phi$), and 7.32 (m, 10, ArH).

Following the above procedure, N-bromo-t-butyloxycarbonyl O-methanesulfonyl thienamycin p-nitrobenzyl ester is obtained when the N-benzyloxycarbonyl thienamycin benzyl ester is replaced by an equivalent amount of N-bromo-t-butyloxycarbonyl thienamycin p-nitrobenzyl ester.

EXAMPLE 6

Benzyl 6-ethylidene-3-(2-benzyloxycarbonylaminoethyl)thio-7-oxo-1-azabicyclo[3.2.0]hept-2-ene-2-carboxylate

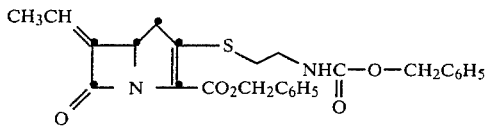

Powdered NaHCO₃ (12.9 mg, 0.154 mmol) is added to a solution of N-benzyloxycarbonyl O-methanesulfonyl thienamycin benzyl ester (44 mg, 0.077 mmol) in anhydrous methanol and the resulting mixture is stirred at 25° C., for 100 minutes. The mixture is diluted with CH₂Cl₂ (15 ml) washed with H₂O (3×5 ml), dried over MgSO₄, filtered, and evaporated in vacuo to an oil (33 mg). This material is purified by tlc on a 250μ×20×20 cm silica gel GF plate, using 3:1 EtOAc-CHCl₃ as developing solvent. The major UV visible band is removed and eluted with EtOAc to give an oil (24 mg). This material is rechromatographed as described to provide benzyl 6-ethylidene-3-(2-benzyloxycarobnylaminoethyl)thio-7-oxo-1-azabicyclo[3.2.0]hept-2-ene-2-carboxylate (16 mg) as a pale yellow oil: ir(CHCl₃) 3610, 1779, 1715, 1508, 1330, 1271, 1178, and 1121 cm⁻¹; nmr (CDCl₃) δ1.80 (d, 3, CH₃), 2.6–3.6 (m, 6, CH₂, SCH₂, NCH₂), 4.68 (d of t, 1, H5), 5.07 (s, 2, NCO₂CH₂φ), 5.28 (s, 2, CO₂CH₂φ), 6.36 (d of q, 1, =CH), and 7.3 (m, 10, ArH); uv (MeOH) 306 (ε6500) nm; mass spectrum m/e 478(M⁺), 410, 343, 269, and 210.

Following the above procedure, p-nitrobenzyl 6-ethylidene-3-(2-bromo-t-butyloxycarbonylaminoethyl)thio-7-oxo-1-azabicyclo[3.2.0]hept-2-ene-2-carboxylate is obtained when the N-benzyloxycarbonyl O-methanesulfonyl thienamycin benzyl ester of Example 6 is replaced by an equivalent amount of N-bromo-t-butyloxycarbonyl O-methanesulfonyl thienamycin p-nitrobenzyl ester from Example 5.

EXAMPLE 7

Benzyl 6-ethyl-3-(2-benzyloxycarbonylaminoethyl)thio-7-oxo-1-azabicyclo[3.2.0]hept-2-ene-2-carboxylate

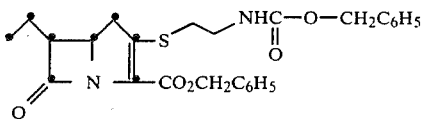

A mixture of benzyl 6-ethylidene-3-(2-benzyloxycarbonylaminoethyl)thio-7-oxo-1-azabicyclo[3.2.0]hept-2-ene-2-carboxylate (15 mg), Bishop PtO₂ (10 mg), and EtOAc (1.5 ml) is hydrogenated in a glass bomb at 40 psi for 2 hrs. More catalyst (5 mg) is added and the hydrogenation is continued for 2 more hours. The mixture is filtered through a packed pad of 1:1 silica gel G—MgSO₄ (1 g of each) using EtOAc (20 ml) as eluant. Evaporation of the EtOAc in vacuo leaves an oil (10 mg) which is purified by tlc on a 250μ×10×15 cm silica gel GF plate using 3:1 EtOAc—CHCl₃ as developing solvent. The major uv visible band at R_f 0.67 is removed and eluted with EtOAc to provide benzyl 6-ethyl-3-(2-benzyloxycarbonylaminoethyl)thio-7-oxo-1-azabicyclo[3.2.0]hept-2-ene-2-carboxylate (4 mg) as an oil: ir(CHCl₃) 3470, 1776, 1715, 1505, 1325, 1276, 1230 and 1125 cm⁻¹; nmr (CDCl₃) δ1.01 (t, 3, CH₂CH₃), 1.77 (m, 2, CH₂, CH₃), 2.8–3.6 (m, 7, CH₂, SCH₂, NCH₂, H6), 4.19 (d of t, H5), 5.09 (s, 2, NCO₂CH₂φ) 5.27 (ABq, 2, CO₂CH₂φ), and 7.32 (m, 10, ArH); uv (MeOH) 316 nm; mass spectrum m/e 480 (M⁺), 410.

Following the above procedures, p-nitrobenzyl 6-ethyl-3-[2-(bromo-t-butoxycarbonylamino)]thio-7-oxo-1-azabicyclo[3.2.0]hept-2-ene-2-carboxylate is obtained when the benzyl 6-ethylidene-3-(2-benzyloxycarbonylaminoethyl)thio-7-oxo-1-azabicyclo[3.2.0]hept-2-ene-2-carboxylate of Example 7 is replaced by an equivalent amount of p-nitrobenzyl 6-ethylidene-3-(2-bromo-t-butyloxycarbonylaminoethyl)thio-7-oxo-1-azabicyclo[3.2.0]hept-2-ene-2-carboxylate.

EXAMPLE 8

6-Ethylidene-3-(2-aminoethyl)thio-7-oxo-1-azabicyclo[3.2.0]hept-2-ene-2-carboxylate

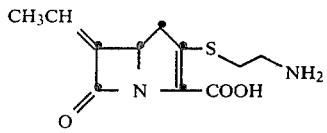

Benzyl 6-ethylidene-3-(2-benzyloxycarbonylaminoethyl)thio-7-oxo-1-azabicyclo[3.2.0]hept-2-ene-2-carboxylate (10 mg) is dissolved in EtOH (4 ml) and treated with 0.1 M pH 7 phosphate buffer (2 ml) and 10% Pd/C (20 mg). The mixture is hydrogenated at atmospheric pressure at 25° C., for 1 hr, and then filtered. The filtrate is concentrated in vacuo to 2 ml and extracted with EtOAc. The aqueous portion is chromatographed on a Dowex-50×4 (sodium form) ion-exchange column, using deionized H₂O as eluting solvent. The desired fractions are combined and lyophilized to afford 6-ethylidene-3-(2-aminoethyl)thio-7-oxo-1-azabicyclo[3.2.0]hept-2-ene-2-carboxylate.

EXAMPLE 9

6-Ethyl-3-(2-aminoethyl)thio-7-oxo-1-azabicyclo[3.2.0]hept-2-ene-2-carboxylic acid

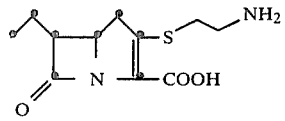

A mixture of benzyl 6-ethyl-3-(2-benzyloxycarbonyl aminoethyl)thio-7-oxo-1-azabicyclo[3.2.0]hept-2-ene-2-carboxylate (10 mg) and 10% Pd/C (20 mg) in 1:1 dioxane-H₂O (4 ml) is hydrogenated at 40 psi for 1 hr. The mixture is filtered to remove the catalyst which is washed with more H₂O (4 ml). The combined filtrate and washings are concentrated in vacuo to 2 ml and loaded onto a column of 200–400 mesh Dowex-50×4 (Na form) ion-exchange resin. The column is eluted with deionized H₂O. The appropriate fractions are pooled and lyophilized to provide 6-ethyl-3-(2-aminoethyl)thio-7-oxo-1-azabicyclo[3.2.0]hept-2-ene-2-carboxylic acid.

EXAMPLE 10

Preparation of Sodium
6-ethyl-3-[2-(bromo-t-butoxycarbonylamino)ethylthio]-7-oxo-1-azabicyclo[3.2.0]hept-2-ene-2-carboxylate

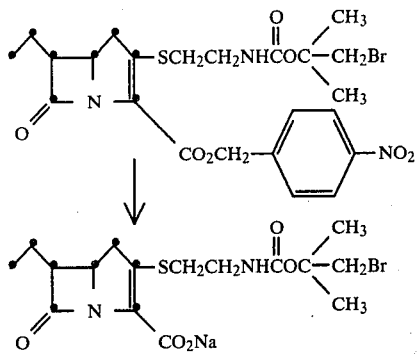

p-Nitrobenzyl 6-ethyl-3-[2-(bromo-t-butoxycarbonylamino)ethylthio]-7-oxo-1-azabicyclo[3.2.0]hept-2-ene-2-carboxylate (20 mg) is dissolved in 4 ml. ethanol. To the solution is added 2 ml pH 8.0, 0.1 M phosphate buffer and 60 mg of 10% Pd/C. The mixture is stirred under 1 atm of $H_2$ at 25° C. for 75 min, and then filtered from the catalyst. The filtrate is neutralized to pH 7.0 with 2.5 N HCl, concentrated to 3 ml and briefly extracted with 5 ml ether. The aqueous solution so obtained contains sodium 6-ethyl-3-[2-(bromo-t-butoxycarbonylamino)ethylthio]-7-oxo-1-azabicyclo[3.2.0-]hept-2-ene-2-carboxylate.

EXAMPLE 11

Preparation of
6-ethyl-3-(2-aminoethyl)thio-7-oxo-1-azabicyclo[3.2.0-]hept-2-ene-2-carboxylate acid

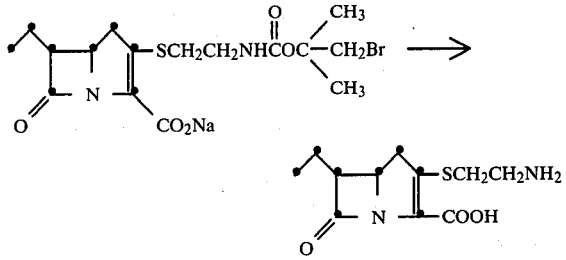

The solution obtained in the previous example which contains sodium 6-ethyl-3-[2-(bromo-t-butoxycarbonylamino)ethylthio]-7-oxo-1-azabicyclo[3.2.0]hept-2-ene-2-carboxylate is heated at 60°–65° C. for 1 hr. The mixture is chromatographed on a Dowex-50×8 (Na form) ion-exchange column which is eluted with water to give the desired 6-ethyl-3-(2-aminoethyl)thio-7-oxo-1-azabicyclo[3.2.0]-hept-2-ene-2-carboxylic acid.

EXAMPLE 12

N-(p-nitrobenzyloxycarbonyl)thienamycin p-nitrobenzyl ester

Thienamycin (140 mg, 0.51 mmol) is dissolved in ice-cold $H_2O$ (35 ml) and the solution is treated with $NaHCO_3$ (428 mg, 5.1 mmol). Dioxane (35 ml) is then added with stirring and ice-bath cooling. After 3 mins, a solution of p-nitrobenzyl chloroformate (165 mg, 0.765 mmol) in dioxane (2 ml) is added dropwise over 2 mins. The resulting mixture is stirred in the cold for 10 mins and then extracted with ice-cold $Et_2O$ (2×20 ml). The aqueous phase is separated, layered with ice-cold EtOAc (35 ml), and acidified to pH 2.3 with 1M $H_2SO_4$ while vigorously stirring in an ice-bath. The layers are separated and the aqueous portion extracted with more cold EtOAc (2×5 ml). The combined EtOAc extracts are washed with ice-cold brine and then extracted thoroughly with 0.05M aq LiOH (10 ml). The LiOH extract is rotary evaporated to remove EtOAc and then lyophilized to provide crude N-(p-nitrobenzyloxycarbonyl) thienamycin lithium salt (288 mg) as a yellow solid.

A portion of the crude lithium carboxylate (250 mg) and p-nitrobenzyl bromide (373 mg, 1.73 mmol) in anhydrous HMPA (2.65 ml) are stirred at room temperature for 105 minutes. The mixture is diluted with EtOAc (60 ml), washed with $H_2O$ (2×50 ml), 5% $NaHCO_3$ (25 ml), $H_2O$ (2×25 ml), and brine (25 ml), dried with $MgSO_4$, filtered, and evaporated i.v. to a yellow solid (423 mg). This material is triturated with $Et_2O$ to remove excess p-nitrobenzyl bromide and the remaining crystals are filtered off and dried i.v. to yield N-(p-nitrobenzyloxycarbonyl) thienamycin p-nitrobenzyl ester (126 mg) as a yellow solid: mp 163.5°–165°; ir (Nujol mull) 1773 and 1690 $cm^{-1}$; nmr (DMSO-$d_6$) δ 1.15 (d, 3, $CH_3$), 2.8–3.6 (m, 7, $CH_2$, $SCH_2$, $NCH_2$, H6), 4.0 (m, 2, H5, H8), 5.22 (s, 2, $NCO_2CH_2Ar$), 5.40 (ABq, 2, $CO_2CH_2Ar$), 7.70 (m, ArH), and 8.27 (m, ArH).

EXAMPLE 13

N-(p-nitrobenzyloxycarbonyl) O-methanesulfonyl thienamycin p-nitrobenzyl ester

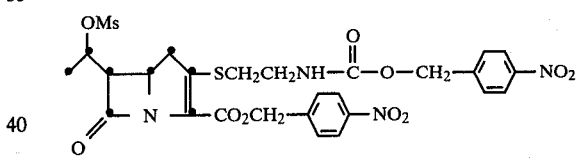

To an ice-cold, stirring solution of N-(p-nitrobenzyloxycarbonyl) thienamycin p-nitrobenzyl ester (186 mg, 0.32 mmol) in anhydrous tetrahydrofuran (THF) (9.5 ml) is added $Et_3N$ (89 µl, 0.64 mmol) and, dropwise over 2 minutes, a solution of methanesulfonyl chloride (55 mg, 0.48 mmol) in THF (1.0 ml) The resulting mixture is stirred in the cold and under $N_2$ for 90 minutes, and then diluted with ice-cold $CH_2Cl_2$ (50 ml). The solution is washed with cold $H_2O$ (20 ml), cold 0.1M pH 3 phosphate buffer (20 ml), and cold 5% $NaHCO_3$ (20 ml), dried with $MgSO_4$, filtered, and evaporated in vacuo to a yellow foam. This material is triturated with anhydrous $Et_2O$ to provide N-(p-nitrobenzyloxycarbonyl) O-methanesulfonyl thienamycin p-nitrobenzyl ester (192 mg) as a pale yellow solid: mp 131°–133°; ir ($CH_2Cl_2$) 1786, 1727, 1522 and 1350 $cm^{-1}$; nmr (DMSO-$d_6$) 1.42 (d, 3, $CH_3$), 2.5–3.4 (m, 7, $CH_2$, $SCH_2$, $NCH_2$, H6), 3.25 (s, 3, $CH_3SO_2$), 3.93 (m, 1, H5), 5.03 (m, 1, H8), 5.20 (s, 2, $NCO_2CH_2Ar$), 5.43 (m, 2, $CO_2CH_2Ar$), 7.63 (m, ArH), and 8.25 (m, ArH); mass spectrum m/e 664 ($M^+$), 578, 500, 415, 372, 304.

Anal., calculated for $C_{27}H_{28}N_4O_{12}S_2$: C, 48.79, H, 4.25; N, 8.43; S, 9.65. Found: C, 49.19; H, 4.36; N, 8.09; S, 9.61.

EXAMPLE 14 p-Nitrobenzyl 6-ethylidene-3-[2-(p-nitrobenzyloxycarbonylamino)ethylthio]-7-oxo-1-azabicyclo[3.2.0]hept-2-ene-3-carboxylate A solution of N-(p-nitrobenzyloxycarbonyl) O-methanesulfonyl thienamycin p-nitrobenzyl ester (50 mg, 0.075 mmol) in anhydrous dioxane (0.75 ml) is treated with anhydrous MeOH (2.5 ml) and NaHCO$_3$ (12.6 mg, 0.15 mmol). The resulting mixture is stirred at room temperature for 17 hours. The precipitate is filtered off, washed with several portions of H$_2$O, and dried in vacuo to yield p-nitrobenzyl 6-ethylidene-3-[2-(p-nitrobenzyloxycarbonylamino) ethylthio]-7-oxo-1-azabicyclo[3.2.0]hept-2-ene-2-carboxylate (32 mg) as a white solid: mp 160°–161°; ir (CH$_2$Cl$_2$) 1779, 1730, 1524, and 1351 cm$^{-1}$; nmr (DMSO-d$_6$) δ 1.86 (d, 3, CH$_3$), 2.8–3.8 (m, 6, CH$_2$, SCH$_2$, NCH$_2$); 4.85 (m, 1, H5), 5.22 (s, 2, NCO$_2$CH$_2$Ar), 5.42 (ABq, 2, CO$_2$CH$_2$Ar), 6.44 (m, 1, =CH), 7.68 (m, ArH), and 8.25 (m, ArH); mass spectrum m/e 500 (M$^+$−68), 415, 304, 256, 239, 223, 209.

EXAMPLE 15

6-Ethyl-3-(2-aminoethyl)thio-7-oxo-1-azabicyclo[3.2.0]hept-2-ene-2-carboxylic acid A mixture of p-nitrobenzyl 6-ethylidene-3-[2-(p-nitrobenzyloxycarbonylamino)ethylthio]-7-oxo-1-azabicyclo[3.2.0]hept-2-ene-2-carboxylate (37 mg), PtO$_2$ (40 mg), THF (4 ml) and EtOH (2 ml) is hydrogenated at 50 psi and 25° C., for 2.5 hrs. The catalyst is filtered off and washed thoroughly with 0.1 M pH 7 phosphate buffer (5 ml). The combined filtrate and washings are concentrated in vacuo to remove most of the organic solvents. The aqueous residue is chromatographed on a column of Dowex-50×4 (Na Form) ion-exchange resin; the product being eluted with deionized H$_2$O. The appropriate fractions are combined and lyophilized to afford 6-ethyl-3-(2-aminoethyl)thio-7-oxo-1-azabicyclo[3.2.0]hept-2-ene-2-carboxylic acid.

EXAMPLE 16

O-Sulfo-Thienamycin

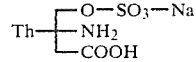

To a solution of 50 mg of N-(p-nitrobenzyloxycarbonyl) thienamycin p-nitrobenzyl ester in 0.5 ml of pyridine is added 20 mg of pyridine sulfuric anhydride. The mixture is allowed to react at 25° for 4 hours then the excess pyridine is removed under reduced pressure. The residue is stirred with 20 ml each of methylene chloride and 0.1% sodium bicarbonate solution for 30 minutes then the aqueous layer is separated and freeze dried. The solid residue containing O-sulfo N-(p-nitrobenzyloxycarbonyl)thienamycin p-nitrobenzyl ester, sodium salt is dissolved in 20 ml of 1:1 aqueous dioxane and hydrogenated for four hours in the presence of 5.0 mg of platinum oxide catalyst at 40 PSIG. The catalyst is filtered and the filtrate is extracted twice with ethylacetate. The aqueous layer is concentrated to 5 ml and chromatographed on 40 ml of XAD-2 resin. The column is eluted with water and the fraction containing O-sulfo thienamycin sodium salt is recovered and freeze dried.

EXAMPLE 17

6-Ethyl-3-(2-aminoethyl)thio-7-oxo-1-azabicyclo[3.2.0]hept-2-ene-2-carboxylic Acid

Step A: p-Nitrobenzyl 6-(1-iodoethyl)-3-[2-(p-nitrobenzyloxycarbonylamino)ethylthio]-7-oxo-1-azabicyclo[3.2.0]hept-2-ene-2-carboxylate A mixture of N-(p-nitrobenzyloxycarbonyl) O-methanesulfonyl thienamycin p-nitrobenzyl ester (66 mg, 0.1 mmol), freshly distilled methyl ethyl ketone (1.5 ml), and powdered sodium iodide (75 mg, 0.5 mmol) is stirred in a capped, thick walled vial with heating in an oil bath maintained at 55°. After stirring and heating for 6 hrs, the mixture is diluted with methylene chloride (20 ml), washed with water (2×10 ml), dilute aqueous sodium thiosulfate solution (10 ml), 5% aqueous sodium bicarbonate solution (10 ml), and brine, dried with magnesium sulfate, filtered, and evaporated under vacuum. The residue is purified by preparative layer chromatography to afford p-nitrobenzyl 6-(1-iodoethyl)-3-[2-(p-nitrobenzyloxycarbonylamino)ethylthio]-7-oxo-1-azabicyclo[3.2.0]hept-2-ene-2-carboxylate as a diastereomeric mixture.

Step B: p-Nitrobenzyl 6-ethyl-3-[2-(p-nitrobenzyloxycarbonylamino)ethylthio]-7-oxo-1-azabicyclo[3.2.0]hept-2-ene-2-carboxylic Acid A sample of p-nitrobenzyl 6-(1-iodoethyl)-3-[2-(p-nitrobenzyloxycarbonylamino)ethylthio]-7-oxo-1-azabicyclo[3.2.0]hept-2-ene-2-carboxylate (35 mg, 0.05 mmol) is dissolved in anhydrous hexamethylphosphoramide (0.5 ml) under a N$_2$ atm. Sodium cyanoborohydride (12.5 mg, 0.2 mmol) is added and the resulting solution is heated under N$_2$ in an oil bath maintained at 70° for 2 hrs. After cooling to room temperature, the reaction mixture is diluted with water (5 ml) and thoroughly extracted with ethyl acetate (5×2 ml). The combined extracts are washed with water and dried, dried with magnesium sulfate, filtered, and evaporated under vacuum. The residue is chromatographed on a silica gel GF plate to provide p-nitrobenzyl 6-ethyl-3-[2-(p-nitrobenzyloxycarbonylamine)ethylthio]-7-oxo-1-azabicyclo[3.2.0]hept-2-ene-2-carboxylate.

Step C: 6-Ethyl-3-(2-aminoethylthio)-7-oxo-1-azabicyclo[3.2.0]hept-2-ene-2-carboxylic Acid A mixture of p-nitrobenzyl 6-ethyl-3-[2-(p-nitrobenzyloxycarbonylamino)ethylthio]-7-oxo-1-azabicyclo-8 3.2.0]hept-2-ene-2-carboxylate (25 mg), dioxane (3 ml), ethanol (0.25 ml), 1M dipotassium hydrogen phosphate (0.05 ml), deionized water (1.75 ml) and 10% palladium on powdered charcoal (25 ml) is hydrogenated at 50 psi for 1 hr. The catalyst is removed by centrifugation and washed with 0.1 M pH 7 phosphate buffer (1 ml) and water (1 ml). The combined supernatant is washed with ethyl acetate (3×3 ml), concentrated in vacuo to ca. 1 ml, and charged onto a Dowex 50-×4 column (sodium form). The column is eluted with deionized water; the progress of the separation is monitored by UV and HPLC. The appropriate fractions are combined, concentrated in vacuo to ca. 2 ml, and lyophilized to give 6-ethyl-3-(2-amino)ethylthio-7-oxo-1-azabicyclo-[3.2.0]hept-2-ene-2-carboxylic acid.

EXAMPLE 18

Preparation of Pharmaceutical Compositions

One such unit dosage form consists in mixing 120 mg 3-(2-aminoethylthio)-6-ethyl-7-oxo-1-azabicyclo[3.2.0]-hept-2-ene-2-carboxylic acid with 20 mg. of lactose and 5 mg. of magnesium stearate and placing the 145 mg mixture into a No. 3 gelatin capsule. Similarly, by employing more of the active ingredient and less lactone, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
| --- | --- |
| 3-(aminoethylthio)-6-ethyl-7-oxo-1-azabicyclo[3.2.0]hept-2-ene-2-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg.) and rough-screen. It is dried at 45° C. and screened again through No. 16 screens. The balance of the cornstarch and the magnesium stearate is added and the mixture is compressed into tablets, approximately 0.5 inch in diameter each weighing 800 mg.

PARENTERAL SOLUTION

Ampoule:
3-(2-aminoethylthio)-6-ethyl-7-oxo-1-azabicyclo[3.2.0]hept-2-ene-2-carboxylic acid—500 mg.
diluent: sterile water for injection—2 ml.

OPTHALMIC SOLUTION 3-(2-aminoethylthio)-6-ethyl-7-oxo-1-azabicyclo[3.2.0]hept-2-ene-2-carboxylic acid—100 mg.
Hydroxypropylmethyl cellulose—5 mg.
Sterile Water—1 ml.

OTIC SOLUTION 3-(2-aminoethylthio)-6-ethyl-7-oxo-1-azabicyclo[3.2.0]hept-2-ene-2-carboxylic acid—100 mg.
Benzalkonium Chloride—0.1 mg.
Sterile Water—1 ml.

TOPICAL OINTMENT 3-(2-aminoethylthio)-6-ethyl-7-oxo-1-azabicyclo[3.2.0]hept-2-ene-2-carboxylic acid—100 mg.
Polyethylene Glycol 4000 U.S.P.—400 mg.
Polyethylene Glycol 400 U.S.P.—1.0 gram The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

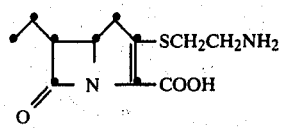

and its pharmaceutically acceptable salts

2. A compound having the structural formula:

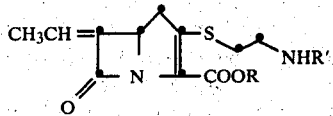

wherein R is a member selected from the group consisting of hydrogen, benzyl and

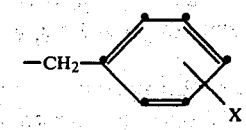

wherein X is a member selected from the group consisting of nitro and lower alkoxy; and R' is a member selected from the group consisting of hydrogen, bromo-t-butoxy-carbonyl, chloro-t-butoxycarbonyl, bromoethoxycarbonyl, benzyloxycarbonyl and p-nitrobenzyloxycarbonyl.

3. A compound according to claim 2 wherein R' and R are hydrogen.

4. A compound having the structural formula:

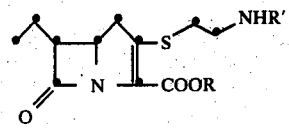

wherein R is a member selected from the group consisting of benzyl and

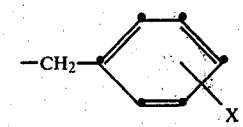

wherein X is a member selected from the group consisting of nitro and loweralkoxy; and R' is a member selected from the group consisting of bromo-t-butoxycarbonyl, chloro-t-butoxycarbonyl, bromoethoxycarbonyl, benzyloxycarbonyl and p-nitrobenzyloxycarbonyl.

5. A process for preparing a compound according to claim 1 which consists essentially of treating a compound of the formula:

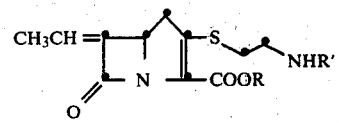

wherein R is a member selected from the group consisting of benzyl and

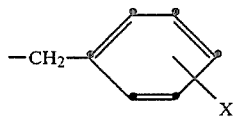

wherein X is a member selected from the group consisting of nitro and loweralkoxy; and R' is a member selected from the group consisting of bromo-t-butoxycarbonyl, chloro-t-butoxycarbonyl, bromoethoxycarbonyl, benzloxycarbonyl and p-nitrobenzyloxycarbonyl, in a suitable organic solvent in the presence of a hydrogenation catalyst and in the presence of 1 to 4 atmospheres of hydrogen at a temperature of from 0° to 25° C. for from 0.5 to 5 hours.

6. An antibiotic pharmaceutical composition consisting essentially of a therapeutically effective amount of a compound according to claim 1 and a pharmaceutical carrier therefor.

7. An antibiotic pharmaceutical composition comprising, in unitary dosage form a therapeutically effective amount of a compound according to claim 1 and a pharmaceutical carrier therefor.

8. A process for preparing a compound according to claim 2 which consists essentially of treating a compound of the formula:

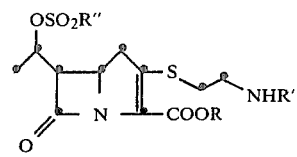

wherein R" is a member selected from the group consisting of loweralkyl, aryl and $O^-M^+$, wherein M is a cation derived from an alkali metal or an organic base, R is a member selected from the group consisting of benzyl and

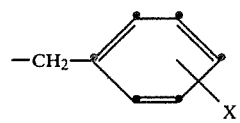

wherein X is a member selected from the group consisting of nitro and loweralkoxy; and R' is a member selected from the group consisting of bromo-t-butoxycarbonyl, chloro-t-butoxycarbonyl, bromoethoxycarbonyl, benzyloxycarbonyl and p-nitrobenzyloxycarbonyl, with a base selected from the group consisting of triethylamine, pyridine, 4-dimethylaminopyridine, and sodium hydride at a temperature of from −15° to 25° C. for 1 to 10 hours.

* * * * *